United States Patent [19]

Irwin

[11] 4,439,596

[45] Mar. 27, 1984

[54] CHLORINATION OF HYDROQUINONE

[75] Inventor: Robert S. Irwin, Wilmington, Del.

[73] Assignee: E. I. Du Pont de Nemours and Company, Wilmington, Del.

[21] Appl. No.: 477,585

[22] Filed: Mar. 21, 1983

[51] Int. Cl.$^3$ .................... C07C 39/24; C08G 63/68
[52] U.S. Cl. .................................. 528/191; 528/193; 528/194; 568/765; 568/774; 568/779
[58] Field of Search ........ 568/726, 774, 765, 776–779; 528/191, 193, 194

[56] References Cited

U.S. PATENT DOCUMENTS 2,748,173 5/1956 Rodgers ............................. 260/623
4,075,119 2/1978 Schmidt et al. .
4,210,765 7/1980 Mark ................................. 568/726

OTHER PUBLICATIONS

Masilamani and Rogic, J. Org. Chem. 1981, 46, pp. 4486–4489.

Primary Examiner—Lester L. Lee

[57] ABSTRACT

Chlorination of hydroquinone by reacting sulfuryl chloride with a slurry or solution of hydroquinone in glacial acetic acid can yield a mixture containing a major proportion of monochlorohydroquinone.

3 Claims, No Drawings

CHLORINATION OF HYDROQUINONE

BACKGROUND OF THE INVENTION

1. Field of the Invention

This invention relates to a new process for chlorinating hydroquinone for coupled acetylation and polymerization with appropriate comonomers to give melt-spinnable anisotropic-melt-forming copolyesters.

2. Description of the Prior Art

U.S. Pat. No. 2,748,173 discloses the reaction of hydroquinone with chlorine in aqueous acetic acid at elevated temperatures to obtain a mixture of hydroquinone and chlorinated hydroquinones.

A statistical mixture of halogenated and non-halogenated bisphenols are said to be obtained by reaction of chlorine and/or bromine with a suspension of a bisphenol in an inert gas or a halogenated hydrocarbon according to U.S. Pat. No. 4,075,119. An improvement over the use of elemental chlorine is said to be achieved by reacting bisphenols with sulfuryl chloride in methylene chloride or benzene according to U.S. Pat. No. 4,210,765.

Masilamani and Rogic, J. Org. Chem., 46, pp. 4486–4489 describe the reaction of phenol with sulfuryl chloride in methylene chloride plus a selected organic "base" to yield a mixture of chlorinated phenols. Reaction of sulfuryl chloride with a bisphenol in ether is also reported in this article.

SUMMARY OF THE INVENTION

One aspect of the present invention is directed to a process for chlorinating hydroquinone to obtain a chlorinated mixture containing a major proportion of monochlorohydroquinone comprising adding sulfuryl chloride to a slurry or solution of hydroquinone and glacial acetic acid, the mole ratio of sulfuryl chloride to hydroquinone being in the range of from about 0.8 to about 1.2. Acetic acid and by-product hydrogen chloride and sulfur dioxide are removed by volatilization. In another aspect of the invention, the resulting chlorinated mixture is acetylated by heating with acetic anhydride to provide an acetylated chlorinated hydroquinone mixture. Appropriate monomers may then be combined and polymerized with the acetylated chlorinated hydroquinone mixture to yield melt-spinnable anisotropic-melt-forming polyesters.

DETAILED DESCRIPTION OF THE INVENTION

The chlorination process of the present invention has a number of advantages. Chlorohydroquinone, i.e. the monochlorohydroquinone, is a desirable monomer for the production of anisotropic-melt-forming polyester (see U.S. Pat. Nos. 4,118,372, and 4,347,349). The present process produces high yields of a mixture having a major proportion, generally in excess of 65 mol % of chlorohydroquinone. The other components of the chlorinated mixture are principally unreacted hydroquinone and dichlorohydroquinones, all of which are compatible with the subsequent acetylation and polymerization reactions. The instant chlorination process produces no significant quantities of undefined by-products which would interfere with subsequent use of the chlorinated mixture in the production of copolyesters as by imparting coloration or causing cross-linking of the polyester with loss of melt-spinnability. The volatile by-products of the chlorination, namely, HCl and $SO_2$, are readily swept from the reaction vessel along with the acetic acid solvent. The chlorinated mixture can therefore be used directly, without purification for the production of polyesters, particularly, anisotropic-melt-forming polyesters. Of course, if pure chlorohydroquinone is desired one can isolate it in pure form by distillation. The chlorinated mixture may be directly acetylated with acetic anhydride for use in polymerization reactions with other monomers. If the acetylated chlorinated mixture is to be used in polymerization, the acetic acid by-product and excess acetic anhydride may be removed either before or after addition of other monomers.

It has been found that the properties of polyester yarns and moldings prepared from the acetylated chlorinated hydroquinone mixtures resulting from this invention are not significantly different from those made from purified chlorohydroquinone. The chlorination conditions selected for the present process may influence yield of the desired chlorohydroquinone to a great extent. Maximum yields of chlorohydroquinone are obtained using a mole ratio of sulfuryl chloride to hydroquinone in the range of from about 0.8 to about 1.2. It is preferred that the ratio of 1.2 not be exceeded by any significant amount because the proportion of polychlorinated hydroquinone increases to undesirable levels and at ratios below 0.8 the proportion of hydroquinone (unreacted) increases to undesirable levels.

The reaction may be carried out with either a slurry or solution of hydroquinone with glacial acetic. Preferably sufficient glacial acetic acid is present to provide a solution of the hydroquinone and the chlorinated reaction product.

The reaction is conveniently carried out at room temperature, and preferably the sulfuryl chloride is added gradually with agitation to avoid excessive concentration of sulfuryl chloride in local spots.

The chlorinated hydroquinone mixture is next acetylated by refluxing with excess acetic anhydride. This reaction releases acetic acid which may be recovered with excess acetic anhydride for recycling.

Comonomers such as terephthalic acid may be added either before or after removal of the excess acetic anhydride and the acetic acid. In either case removal is achieved by distillation before full polymerization is achieved. The succeeding steps in melt polymerization follow normal procedures.

The resulting polymer may be melt spun into fiber or if desired, melt-extruded into bars or molded into shaped articles. Physical properties were determined as follows:

Monofilament tensile properties were measured using a recording stress-strain analyzer at 70° F. (21.1° C.) and 65% relative humidity. Gauge length was 1.0 in (2.54 cm), and rate of elongation was 10%/min. Results are reported as D/T/E/M or T/E/M where D is linear density in tex units, T is break tenacity in dN/tex, E is elongation-at-break expressed as the percentage by which initial length increased, and M is initial tensile modulus in dN/tex. Average tensile properties for three to five filament samples are reported.

Tensile properties of molded polymers were measured by ASTM Method D638-76 on injection molded specimens with a narrow neck section. The specimens are prepared by injection molding from a one-ounce (28 g) ram machine at a barrel temperature of about 270° to 290° C. as described in Example 2.

The examples which follow illustrate various aspects of the present invention but are not intended to limit the invention in any respect.

EXAMPLE 1

This example shows preparation of a mixture of chlorinated hydroquinones and conversion to the corresponding diacetates. The acetylated chloro mixture (ACM) was blended with terephthalic acid (T) and 6-acetoxy-2-naphthoic acid (ANA) before removal of excess acetic anhydride and of acetic acid. After subsequent removal of these volatiles and melt polymerization of the remainder a polymer having the approximate molar composition ACM/T/ANA (42.5/42.5/15) was obtained.

A 1 liter flask equipped with stirrer, dropping funnel, nitrogen inlet and venting outlet was charged with 55.0 g (0.50 mole) of hydroquinone and 500 ml glacial acetic acid. After stirring to effect partial solution, 40.5 ml (67.5 g, 0.50 mole) of sulfuryl chloride was added over 1.5 hours with stirring. On completion of the addition, the reaction mixture was allowed to stand for one hour, after which the solvent and residual HCl and SO$_2$ were stripped in vacuo, with minimum heating in a rotary evaporator by use of a water jet aspirator. A slightly off-white solid weighing 74.0 g was obtained. The mixture was found by gas chromatography to contain by weight 79.46% chlorohydroquinone, 12.88% dichlorohydroquinone, and 7.66% hydroquinone; other by-products, essentially zero.

A 250 ml 3-necked flask equipped with a glass stirrer extending through a pressure-tight resin bushing, a nitrogen inlet and a short Vigreux column leading to a water-cooled condenser and flask for collecting acetic acid was charged with a 13.32 g portion of the above chlorinated mixture and 40 ml of acetic anhydride and the mixture was heated to reflux for 3 hours. Thereafter 14.11 g of terephthalic acid (0.085 mole) and 6.90 g (0.03 mole) of 6-acetoxy-2-naphthoic acid were added and the mixture was stirred and heated by a Wood's metal bath at bath temperatures which were increased from 150° C. to 320° C. in 107 min. Acetic anhydride and acetic acid were collected. The pressure then was reduced by means of a vacuum pump to 2.5 mm Hg and further reduced to 0.2 to 0.5 mm Hg in the next 6 minutes while the bath temperature was maintained at 320° C. to 330° C. The flask was cooled; the polymer isolated. The polymer softened on a hot bar at 270° C. and long fibers could be pulled from the melt at 315° C. A molded plug of the polymer was melt spun through a 0.23 mm orifice and a bobbin of monofilament yarn was collected at 549 m/min when the cell and spinneret temperatures were both 300° C. The yarn was heat treated relaxed in an oven purged with nitrogen and heated from 180° C. to 282° C. in 4 hours and at 282° C. for 16 hours.

See Table 1 for properties of the filaments before and after heat treatment.

EXAMPLE 2

This example shows preparation of a mixture of chlorinated hydroquinones, followed by blending with 4,4'-dihydroxybiphenyl (DHB), terephthalic acid (T) and isophthalic acid (I), acetylation and melt polymerization. A polymer having the approximate molar composition ACM/DHB/T/I (40/10/40/10) was obtained.

A 2-liter glass resin kettle equipped with a Hastalloy® C stirrer operating through a resin bearing and monitored with a torque meter, a reflux/take-off condenser, addition funnel and exit port was charged with 1 liter glacial acetic acid and 244.2 g (2.22 moles, 5% excess) of hydroquinone. To the stirred mixture at room temperature and under nitrogen was added dropwise 181.1 ml (299.7 g, 2.22 moles) of sulfuryl chloride. The addition was completed in 118 min and the reaction was stirred an additional 30 min.; thereafter the kettle was heated to 170° C. to distill off acetic acid; then the heat was removed and the kettle evacuated to complete the distillation. After 1.5 hours the cooled kettle was brought to atmospheric pressure and 104.16 g (0.56 mole, 5% excess) of 4,4'-dihydroxybiphenyl, 351.92 g (2.12 mole) terephthalic acid and 87.98 g (0.53 mole) isophthalic acid was added. The kettle was evacuated and purged three times with argon whereupon 0.6 g of sodium acetate and 624 g of acetic anhydride were added. The reaction mixture was heated by immersing slowly in a Wood's metal bath and stirred with a continuous argon purge at an initial bath temperature of 261° C. which was increased slowly to 300° C. in 100 min. while continually removing acetic acid. The pressure then was slowly reduced to 1.2 mm Hg in 35 min while the bath temperature was increased to 339° C. at which time the argon flow was stopped. Heating and stirring was continued for 42 min until a rise in torque of 0.9 in-lb was observed. The bath temperature varied from 338° C. to 341° C.; the pressure, from 0.8 to 1.4 mm Hg. The flask was cooled; the polymer isolated. Yield was 752 g, 99%. Fibers could be pulled from the melt at 314° C. The polymer was comminuted, washed with chloroform and dried at 100° C. in vacuo.

Microtensile bars of this polymer and a control polymer of the same composition made similarly but with use of pure chlorohydroquinone were prepared by extrusion in a 1 oz ram machine at a barrel temperature of 270°–290° C., 2.1 to 2.8 MPa pressure, a slow ram speed and a 20/10 sec. cycle into a V-block mold held at room temperature. Bars were 6.35 cm long by 0.16 cm thick and the neck point was 0.325 cm wide. The tensile properties of bars made from this polymer were equivalent to those prepared from the control polymer of comparable molecular weight.

Properties are shown in Table 2.

TABLE 1

| Fibers from ACM/T/ANA (42.5/42.5/15) | | | | |
|---|---|---|---|---|
| Fiber | Tenacity T (dN/tex) | Elongation E (%) | Modulus M(dN/tex) | tex |
| As-spun | 4.0 | 1.4 | 338 | 0.82 |
| Heat treated | 13.8 | 4.0 | 389 | 0.59 |

TABLE 2

| Injection Moldings from ACM (or ClHQ)/DHB/T/I (40/10/40/10) | | | | |
|---|---|---|---|---|
| | | Tensile Properties (Standard Deviation) | | |
| Composition | No. Tested | Strength, MPa | Elongation (%) | Modulus, GPa |
| Polymer from ACM | 6 | 159 (23) | 1.22 (0.21) | 17 (3) |
| Polymer from purified chlorohydroquinone (ClHQ) | 4 | 161 (14) | 1.45 (0.23) | 15 (1) |

What is claimed is:

1. A process for chlorinating hydroquinone to obtain a chlorinated mixture containing a major proportion of chlorohydroquinone comprising adding sulfuryl chloride to a slurry or solution of hydroquinone and glacial acetic acid, the mole ratio of sulfuryl chloride to hydroquinone being in the range of from about 0.8 to about 1.2.

2. The process of claim 1 wherein enough glacial acetic acid is present to provide a solution of the hydroquinone and chlorinated reaction product.

3. In a process for preparing a melt-spinnable anisotropic-melt forming polyester by reacting chlorohydroquinone with other monomers, the improvement comprising adding sulfuryl chloride to a slurry or solution of hydroquinone and glacial acetic acid, the mole ratio of sulfuryl chloride to hydroquinone being in the range of from about 0.8 to about 1.2 to obtain a chlorinated mixture, acetylating the mixture by heating with acetic anhydride, adding appropriate monomers and polymerizing the mixture.

* * * * *